(12) United States Patent
Byström et al.

(10) Patent No.: US 6,498,182 B2
(45) Date of Patent: Dec. 24, 2002

(54) COMPOUNDS

(75) Inventors: Styrbjörn Byström, Täby (SE); Stephen James, Vällingby (SE); Charlotta Liljebris, Knivsta (SE)

(73) Assignee: Biovitrum AB, Stockholm (SE)

( * ) Notice: Subject to any disclaimer, the term of this patent is extended or adjusted under 35 U.S.C. 154(b) by 1 day.

(21) Appl. No.: 09/963,773

(22) Filed: Sep. 26, 2001

(65) Prior Publication Data

US 2002/0061921 A1 May 23, 2002

Related U.S. Application Data

(60) Provisional application No. 60/238,896, filed on Oct. 10, 2000, and provisional application No. 60/300,886, filed on Jun. 26, 2001.

(30) Foreign Application Priority Data

Sep. 26, 2000 (SE) .............................. 0003437
Jun. 13, 2001 (SE) .............................. 0102094

(51) Int. Cl.[7] .................... A61K 31/404; C07D 209/56; A61P 3/10
(52) U.S. Cl. ........................ 514/411; 548/450
(58) Field of Search ............................ 548/450; 514/411

(56) References Cited

U.S. PATENT DOCUMENTS 4,510,157 A 4/1985 Asselin et al. .............. 514/411

FOREIGN PATENT DOCUMENTS

| WO | WO 96/40113 | 12/1996 | ......... A61K/31/38 |
| WO | WO 97/08934 | 3/1997 | |
| WO | WO 98/27065 | 6/1998 | ......... C07D/233/70 |
| WO | WO 99/58519 | 11/1999 | ......... C07D/307/80 |
| WO | WO 99/58521 | 11/1999 | ......... C07D/333/74 |
| WO | WO 99/61435 | 12/1999 | ......... C07D/333/74 |

OTHER PUBLICATIONS

Siegfried Petersen, et al. *Oxim und Acylhydrazone des 2–(1,4–Naphthochinon–2–yl)–2–methyl–propionaldehyds.* Liebigs Ann. Chem. 764, 50–57 (1972).

Susan P. Rohrer, et al. *Identification and characterization of subtype selective somatostatin receptor agonists.* J. Physiol. (Paris) 94 (2000) 211–215.

*Primary Examiner*—Joseph K. McKane
*Assistant Examiner*—Andrea D. Small
(74) *Attorney, Agent, or Firm*—Fish & Richardson P.C.

(57) ABSTRACT

The present invention is directed to compounds of formula I, formula Ia, and formula Ib.

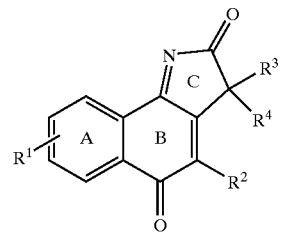

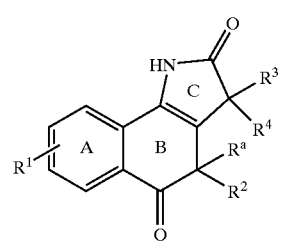

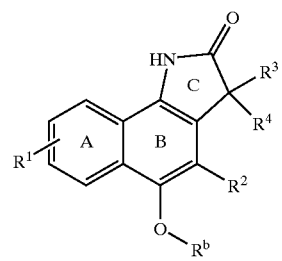

wherein each of $R^1$, $R^2$, $R^3$, $R^4$, $R^a$, and $R^b$ has been defined herein. The invention is also directed to a process for the preparation, the use and pharmaceutical compositions comprising the compounds described above. These novel compounds are useful in therapy, particularly for the treatment of type 2 diabetes.

24 Claims, No Drawings

COMPOUNDS

CROSS REFERENCE TO RELATED APPLICATIONS

This application claims priority from Swedish Patent Application No. 0003437-1, filed Sep. 26, 2000; U.S. Provisional Patent Application Serial No. 60/238,896, filed Oct. 10, 2000; the Swedish Patent Application No. 0102094-0 filed Jun. 13, 2001; and U.S. Provisional Patent Application No. 60/300,886, filed Jun. 26, 2001. These applications are incorporated herein by reference in their entirety.

TECHNICAL FIELD

The present invention is directed to novel compounds, to a process for their preparation, their use and pharmaceutical compositions comprising said novel compounds. These novel compounds are useful in therapy, particularly for the treatment of type 2 diabetes.

BACKGROUND

Phosphorylation on serine, threonine and tyrosine amino acid residues in downstream proteins forms the major output from growth factor and cytokine receptors, from which a cellular response is built. A large number of growth factor and cytokine-regulated protein tyrosine kinases (PTKs) have been identified which can be integral parts of receptor proteins or cytosolic molecules (Al-Obeidi, FA, Wu, JJ & Lam, KS, Biopolym. Pept. Sci. Sect. 47, 197–223). These serve to phosphorylate proteins on tyrosine residues within specific primary amino acid sequences which, when phosphorylated, act as docking points for proteins that contain SH2 domains. It is the docking of proteins to phosphorylated tyrosine residues that contributes to the activation of such proteins and the establishment of a signal transduction cascade.

The overall output from signal transduction cascades is derived from the balance between phosphorylation and dephosphorylation of proteins. Phosphotyrosines are returned to their free acid form by the action of protein tyrosine phosphatases (PTPs) (Zhang, Z Y (1998) Crit. Rev. Biochem. Mol. Biol., 33, 1–52). Whilst a large number of PTKs has been identified (Hunter, T (1994) Sem. Cell Biol. 5, 367–376), the number of PTPs identified to date is decidedly smaller (van Huijsduijnen, R H (1998) Gene 225, 1–8). Despite the smaller number of enzymes in the PTP family available for investigation, a detailed understanding of the roles they play in signal transduction and disease has not been forthcoming. This is due in part to the lack of small molecule inhibitor molecules which are specific for members of the PTP family and which are permeable to the cell membrane and can thus be used in cell-based experiments. Furthermore, whilst experiments in transgenic animals can be and have been performed in which individual PTPs can be ablated, the effects of the loss of function of a specific enzyme may be masked by compensation by other members of the PTP family. Thus, the availability of small molecule inhibitors of PTPs would be very useful to the study of this important family of enzymes.

A role for the PTP family of proteins in ontogeny and disease is now becoming clearer (Li, L & Dixon, J E (2000) Sem. Immunol. 12, 75–84). Thus, experiments with gene knockouts in transgenic animals has revealed that the motheaten phenotype of mice in which cells of the haematopoietic lineage undergo hyper-proliferation is due to the loss of normal SHPTP1 function (Schultz, L D, Schweitzer, P A, Rajan, T V, Yi, T & Ihle, J N (1993) Cell 73, 1445–1454). Loss of function in the receptor-like subfamily of PTPs leads to conditions such as heightened and reduced sensitivity to insulin (Ren, J-M, Li, P-M, Zhang, W-R, Sweet, L J, Cline, G, Shulman, G I, Livingston, J N & Goldstein, B J (1998) Diabetes 47, 493–497), stunted growth and neurological disruption (Elchelby, M, Wagner, J, Kennedy, T E, Lanctot, C, Michaliszyn, E, Itie, A, Drouin, J & Tremblay, M L (1999) Nature Genet. 21, 330–333) and blockages in T cell maturation (Kishihara, K, Penninger, J, Wallaca, V A, Kundig, T M, Kawai, K, Wakeham, A, Timms, E, Pfeffer K, Ohashi, P S & Thomas P L (1993) Cell 74, 143–156).

The recent descriptions of mice in which the PTP PTP1B had been disrupted revealed that loss of function of this enzyme leads to enhanced insulin sensitivity and resistance to the development of obesity, thus revealing a therapeutic need for the development of specific PTP inhibitors (Elchelby, M, Payette, P, Michaliszyn, E, Cromlish, W, Collins, S, Loy, A L, Normandin, D, Cheng, A, Himms.Hagen, J, Chan, C C, Ramachandran, C, Gresser, M J, Tremblay, M L & Kennedy, B P (1999) Science 283, 1544–1548; Klaman, L D, Boss, O, Peroni, O D, Kim, J K, Martino, J L, Zablotny, J M, Moghal, N, Lubkin, M, Kim, Y-B, Sharpe, A H, Stricker-Krongrad, A, Shulman, G I, Neel, B G & Kahn, B B (2000) Mol. Cell. Biol. 20, 5479–5489). The mechanism of insulin action depends critically upon the phosphorylation of tyrosine residues in several proteins in the insulin signaling cascade. PTPs that dephosphorylate these proteins are important negative regulators of insulin action. Therefore, the use of specific PTP inhibitors may therapeutically enhance insulin action.

The anabolic effects of insulin are triggered through the activation of a variety of signal transduction cascades which lie downstream of the insulin receptor (Gustafson, T. A., Moodie, S A & Lavan, B E (1999) Rev. Physiol. Biochem. Pharmacol. 137, 71–190). The varieties of signals that are activated by insulin are thought to contribute to the range of effects that insulin controls. However, each pathway is activated by a common series of biochemical reactions proximal to the insulin receptor. Thus, the insulin receptor undergoes autophosphorylation on tyrosine residues when activated by insulin, and also phosphorylates other proteins, in particular, the insulin receptor substrate proteins (IRSs). It has now become widely accepted that the resistance to insulin that is a feature of type 2 diabetes results in part from dysfunctions in signal transduction activated by the insulin receptor, in particular in steps early in the signaling cascades which are common to different pathways (Virkamäki, A, Ueki, K & Kahn, R C (1999) J. Clin. Invest 103, 931–943; Kellerer, M, Lammers, R & Häring, H-U (1999) Exp. Clin. Endocrinol. Diabetes 107, 97–106).

The signals that emanate from the insulin receptor are switched off by the returning of the insulin receptor and other components of the signal transduction cascades to their basal, non-active states. For the insulin receptor and the IRS proteins, this is achieved by dephosphorylation of phosphotyrosine residues. It is now becoming clear that different PTPs may regulate the insulin receptor in different tissues, but the number of candidate enzymes which do this is small (Wälchi, S., Curchod, M-L., Pescini Gobert, R., Arkinstall, S. & Hooft van Huijsduijnen, R. (2000) J. Biol. Chem. 275, 9792–9796). Thus, protein tyrosine phosphatase 1B (PTP1B) appears to be the major negative regulator of the insulin receptor in muscle and liver tissues (see for example Elchelby, M, Payette, P, Michalszyn, E, Cromlish, W, Collins, S, Loy, A L, Normandin, D, Cheng, A, Himms-Hagen, J, Chan, C—C, Ramachandran, C, Gresser, M J, Tremblay, M & Kennedy, B P (1999) Science, 283, 1544–1548; Goldstein, B J, Bittner-Kowalczyk, A, White, M F & Harbeck, M (2000) J. Biol. Chem. 275, 4283–4289). By contrast, PTP alpha may play a more dominant role in regulating the insulin receptor in adipose tissue (Calera, M R, Vallega, G & Pilch, P F (2000) J. Biol. Chem. 275 6308–6312).

The development of type 2 diabetes is characterised by a protracted period of insulin resistance. In human subjects who are obese and insulin resistant, PTP protein concentrations are increased, which has led to the idea that elevations in the proteins contributes to the cause of the diabetic state (Ahmad, F, Azevedo, J L, Cortright, R, Dohm, G L & Goldstein, B J (1997) J. Clin. Invest. 100 449–458). The two most significantly elevated are PTP1B and LAR. Considering that loss of LAR activity is associated with insulin resistance and diabetes (Ren, J-M, Li, P-M, Zhang, W-R, Sweet, L J, Cline, G, Shulman, G I, Livingston, J N & Goldstein, B J (1998) Diabetes 47 493–497), these data support the concept that PTP1B is a major contributor to the insulin resistant state and that pharmacological inhibition of its activity may go some way towards pharmaceutically alleviating the condition. Indeed, the recent reports of the knockout mouse in which PTP1B has been ablated confirm that loss of PTP1B activity leads to enhancement of the metabolic effects of insulin (Elechelby, M, Payette, P, Michalszyn, E, Cromlish, W, Collins, S, Loy, AL, Normandin, D, Cheng, A, Himms-Hagen, J, Chan, C-C, Ramachandran, C, Gresser, M J, Tremblay, M & Kennedy, B P (1999) Science, 283, 1544–1548; Klaman, L D, Ross, O, Peroni, O D, Kim, J K, Martino, J L, Zabolotny, J M, Moghal, N, Lubkin, M, Kim, Y-B, Sharpe, A H, Stricker-Krongrad, A, Shulman, G I, Neel, B G & Kahn, B B (2000) Mol. Cell. Biol. 20 5479–5489). Furthermore, inhibition of PTP1B with a specific small molecule has been reported to treat the symptoms of diabetes in the ob/ob mouse (Wrobel, J, Sredy, J, Moxham, C, Dietrich, A, Li, Z, Sawicki, D R, Seestaller, L, Wu. L, Katz, A, Sullivan, D, Tio, C & Zhang, Z-Y (1999) J. Med. Chem. 42 3199–3202).

The patent application with the publication no. WO 96/40113, discloses heterocyclic nitrogen containing compounds, such as nitropyridine or nitrothiazole, capable of inhibiting protein tyrosine phosphatase activity. Such molecules are disclosed as being useful to modulate or regulate signal transduction by inhibiting protein tyrosine phosphatase activity and to treat various disease states including diabetes mellitus.

WO 98/27065 discloses a class of compounds which are stated as being protein tyrosine phosphatase modulating compounds. These prior art compounds are however structurally distinct from the compounds claimed in the present patent application.

WO 97/08934 discloses aryl acrylic acid compounds of a certain structure, which compounds are stated as having protein tyrosine protease modulating activity. Also these prior art compounds are however structurally distinct from the compounds claimed in the present patent application.

WO 99/58519 discloses certain phenyl oxo-acetic acid compounds. These compounds are stated as being useful in the treatment of metabolic disorders related to insulin resistance and hyperglycemia. Also these prior art compounds are however structurally distinct from the compounds claimed in the present patent application.

WO 99/58521 discloses the use of 11-aryl-benzo[b]naphtho[2,3-d]furan and 11-aryl-benzo[b]naphtho[2,3-d]thiophene compounds to inhibit protein tyrosine phosphatase activity. Such compounds are disclosed as being useful to modulate or regulate signal transduction by inhibiting protein tyrosine phosphatase activity and to treat various disease states including diabetes mellitus.

The preparation of the compound 4-hydroxy-3,3-dimethyl-2H-benzo[g]indole-2,5(3H)-dione, said compound having the chemical structure

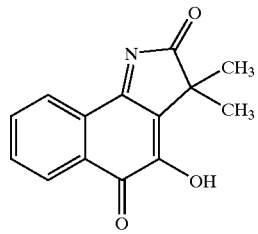

is disclosed by Siegfried Petersen et al. in *Justus Liebigs Ann. Chem.* (1972), 764, pp. 50–57. However, this prior art document does not disclose or even suggest that this compound may have therapeutic activity, and particularly not in the diabetes area, such as type 2 diabetes.

The object of the present invention was to provide novel compounds having improved advantages over drugs currently used for the treatment of type 2 diabetes. It should be appreciated that the wording "improved advantages" is not necessarily defined as more potent compounds, but as compounds having improved advantages overall, including but not limited to also improved selectivity and less side-effects.

DISCLOSURE OF THE INVENTION

The novel compounds according to the present invention are defined by the general formula I

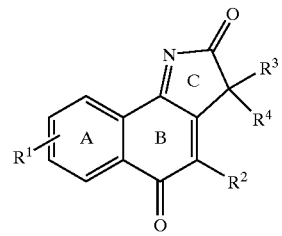

wherein
R$^1$ is
(i) hydrogen;
(ii) linear or branched C$_1$–C$_6$ alkoxy;
(ii) —O—(C$_1$–C$_6$ alkyl)—Q, where the alkyl group may be linear or branched, and where Q is phenyl, naphthyl, or a heterocycle having from 5 and up to 10 ring atoms, where at least one of the ring atoms is an atom other than carbon, such as O, N, or S (e.g., R$^1$ can be —O-methyl-phenyl, —O-ethyl-phenyl, or —O-propyl-phenyl); and (iii)

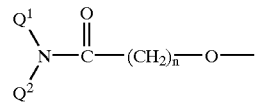

where n is an integer 1 or 2; and each of Q$^1$ and Q$^2$ is independently hydrogen or C$_1$–C$_6$ alkyl where the alkyl group may be linear or branched (e.g., methyl or ethyl); or

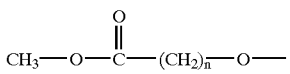

(iv)

where n is an integer 1 or 2;
R² is
(i) hydroxy;
(ii) linear or branched $C_1$–$C_6$ alkoxy (e.g., $C_1$–$C_3$ alkoxy);
(iii) —O—CO—($C_1$–$C_6$ alkyl) where the alkyl group may be linear or branched (e.g., —O—CO-methyl or —O—CO-methyl); or
(iv) —O—CO-phenyl, or —O—CO-naphthyl;
each of R³ and R⁴ is independently
(i) $C_1$–$C_6$ alkyl, where the alkyl group may be linear or branched (e.g., methyl or ethyl); or
(ii) cyclopentane, or cyclohexane;
the compound 4-hydroxy-3,3-dimethyl-2H-benzo[g]indole-2,5(3H)-dione being excluded.

The invention also features compounds of formula Ia

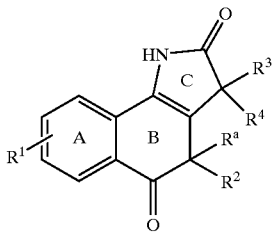

Ia wherein each of R¹, R², R³ and R⁴ has been defined in formula I above, and wherein $R^a$ is —CH₂—CO—($C_1$–$C_6$ alkyl) where the alkyl group may be linear or branched (e.g., —CH₂—CO-methyl or —CH₂—CO-ethyl);

The invention further features compounds of formula Ib

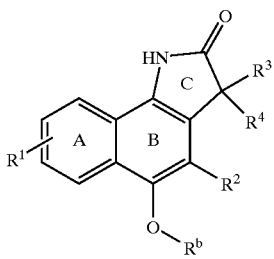

Ib wherein each of R¹, R², R³ and R⁴ has been defined in formula I above, and wherein $R^b$ is
(i) —CO—($C_1$–$C_6$ alkyl) where the alkyl group may be linear or branched (e.g., —CO-methyl or —CO-ethyl); or
(ii) hydrogen.

Within the scope of the invention are also pharmaceutically and pharmacologically acceptable salts of a compound of formula I, formula Ia, and formula Ib, as well as hydrates thereof.

Some specific examples of R¹ in accordance with the present invention are hydrogen, methoxy, ethoxy, propoxy, butoxy, pentoxy, and hexyloxy, wherein said alkoxy substituents may be linear or branched. Another specific example of R¹ in accordance with the present invention is phenyl-(CH₂)$_n$—O— where n is an integer 1, or 2. Still another specific example of R¹ in accordance with the invention is H₂N—CO—CH₂—O—.

Some specific examples of R² in accordance with the present invention are hydroxy; methoxy, ethoxy, propoxy, butoxy, pentoxy, and hexyloxy, wherein said alkoxy substituents may be linear or branched; —O—CO—(CH₂)$_n$—CH₃ wherein n is an integer 0, 1, 2, 3, 4 or 5 (e.g., —O—CO—CH₂—CH₃); —O—CO-phenyl; and —O—CO-naphthyl.

Some specific examples of R³ and R⁴ in accordance with the present invention are methyl, ethyl, propyl, butyl, pentyl, and hexyl, wherein the alkyl groups may be linear or branched; cyclopentyl; and cyclohexyl.

A specific example of $R^a$ in accordance with the present invention is —CH₂—CO—(CH₂)$_n$—CH₃ wherein n is an integer 0, 1, 2, 3, 4 or 5 (e.g., —CH₂—CO—CH₂—CH₃, —CH₂—CO—(CH₂)₂—CH₃, or —CH₂—CO—(CH₂)₃—CH₃).

A specific example of $R^b$ in accordance with the present invention is —CO—(CH₂)$_n$—CH₃ wherein n is an integer 0, 1, 2, 3, 4 or 5 (e.g., —CO—CH₃, —CO—CH₂—CH₃, or —CO—(CH₂)₂—CH₃).

A subset of the compounds of the invention include compounds of formula I, formula Ia, or formula Ib wherein R¹ is linear or branched $C_1$–$C_6$ alkoxy, phenyl-(CH₂)$_n$—O— where n is an integer 1 or 2, or H₂N—CO—CH₂—O—; and R² is linear or branched $C_1$–$C_6$ alkoxy, —O—CO—(CH₂)$_n$—CH₃ where n is an integer 0, 1, 2, 3, 4 or 5, —O—CO-phenyl, or —O—CO-naphthyl. Another subset of compounds of the invention include compounds of formula I, formula Ia, or formula Ib wherein R¹ is hydrogen, linear or branched $C_1$–$C_6$ alkoxy, phenyl-(CH₂)$_n$—O— where n is an integer 1 or 2, or H₂N—CO—CH₂—O—; R² is hydroxy, linear or branched $C_1$–$C_3$ alkoxy, or —O—CO—(CH₂)$_n$—CH₃ where n is an integer 0, 1, 2, or 3; and R³ and R⁴ are each and independently linear or branched $C_1$–$C_3$ alkyl. Still another subset of the invention include compounds of formula I, formula Ia, or formula Ib wherein R¹ is hydrogen, linear or branched ethoxy, propoxy, or butoxy; phenyl-(CH₂)$_n$—O— where n is an integer 1 or 2; or H₂N—CO—CH₂—O—; R² is hydroxy; methoxy, —O—CO—CH₃; R³ and R⁴ are each methyl; $R^a$ is —CH₂—CO—CH₃; and $R^b$ is —CO—CH₃.

The compounds according to the present invention are useful in therapy, particularly for the treatment of type 2 diabetes mellitus.

Also within the scope of the invention is the use of a compound of the formula I, for the manufacture of a medicament for the treatment of type 2 diabetes mellitus.

A further aspect of the invention is the use of a compound of the formula Ia, for the manufacture of a medicament for the treatment of type 2 diabetes mellitus.

Still a further aspect of the invention is the use of a compound of the formula Ib, for the manufacture of a medicament for the treatment of type 2 diabetes mellitus.

A further aspect of the invention is a method for the treatment of a patient suffering from type 2 diabetes mellitus, whereby an effective amount of a compound according to formula I above, is administered to a patient in need of such treatment.

A further aspect of the invention is a method for the treatment of a patient suffering from type 2 diabetes mellitus, whereby an effective amount of a compound according to formula Ia above, is administered to a patient in need of such treatment.

Still a further aspect of the invention is a method for the treatment of a patient suffering from type 2 diabetes mellitus, whereby an effective amount of a compound according to formula Ib above, is administered to a patient in need of such treatment.

DEFINITIONS

As used herein, an alkyl is a straight or branched hydrocarbon chain containing the indicated number of carbon atoms. Examples of alkyl groups include, but are not limited to, methyl, ethyl, propyl, isopropyl, butyl, isobutyl, sec-butyl, tert-butyl, n-pentyl, 2-methylpentyl, and n-hexyl.

By cycloalkyl is meant a cyclic alkyl group containing the indicated number of carbon atoms. Some examples of cycloalkyl are cyclopropyl, cyclopentyl, cyclohexyl, adamantyl, and norbornyl. Heterocycloalkyl is a cycloalkyl group containing the indicated number of heteroatoms such as nitrogen, oxygen, or sulfur. Examples of heterocycloalkyl include piperidinyl, piperazinyl, tetrahydropyranyl, tetrahydrofuryl, and morpholinyl.

As used herein, aryl is an aromatic group containing the indicated number of ring atoms. Examples of an aryl group include phenyl, naphthyl, phenanthryl, and anthracyl. Heteroaryl is aryl containing the indicated number of heteroatoms such as nitrogen, oxygen, or sulfur. Some examples of heteroaryl are pyridyl, furanyl, pyrrolyl, thienyl, thiazolyl, oxazolyl, and imidazolyl.

Each of the cycloalkyl, heterocycloalkyl, aryl, or heteroaryl groups described herein is optionally substituted with $C_{1-4}$ alkyl, $C_{3-6}$ cycloalkyl, 3–6 membered heterocycloalkyl, $C_{6-10}$ aryl, 6–10 membered heteroaryl, $C_{7-14}$ aralkyl, $C_{1-4}$ alkyl-heteroaryl with 6–10 ring atoms, $C_{1-4}$ alkoxy, hydroxy, hydroxyl-$C_{1-4}$ alkyl, carboxyl, halo, halo-$C_{1-4}$ alkyl, amino, amino-$C_{1-4}$ alkyl, nitro, cyano, $C_{1-5}$ alkylcarbonyloxy, $C_{1-5}$ alkyloxycarbonyl, $C_{1-5}$ alkylcarbonyl, formyl, oxo, aminocarbonyl, $C_{1-5}$ alkylcarbonylamino, $C_{1-4}$ alkylsulfonylamino, aminosulfonyl, aminocarbonyloxy, or $C_{1-4}$ alkyloxycarbonylamino.

Note that an amino group can be unsubstituted, mono-substituted, or di-substituted. It can be substituted with groups such as $C_{1-4}$ alkyl, $C_{3-6}$ cycloalkyl, 3–6 membered heterocycloalkyl, $C_{6-10}$ aryl, or 6–10 membered heteroaryl. Halo refers to fluoro, chloro, bromo, or iodo.

METHODS OF PREPARATION

The compounds according to the present invention may be prepared as described by the following methods.

The compounds of formula I can be synthesized from the corresponding 5 and 6-hydroxyquinone according to the procedure reported by Ley and Nast *Angew. Chem.* 1967, 79, 150 (see Schemes 1 and 2 below). The starting material 5-hydroxyquinone is commercially available from Aldrich. Another starting material silver oxide can be prepared according to a literature procedure (*Vogel's textbook of practical Organic Chemistry* $5^{Th}$ Edition, p677) and stored under inert atmosphere in the dark until used. Freshly prepared silver oxide generally gives the best results.

SCHEME 1

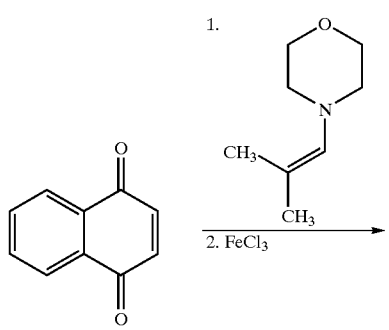

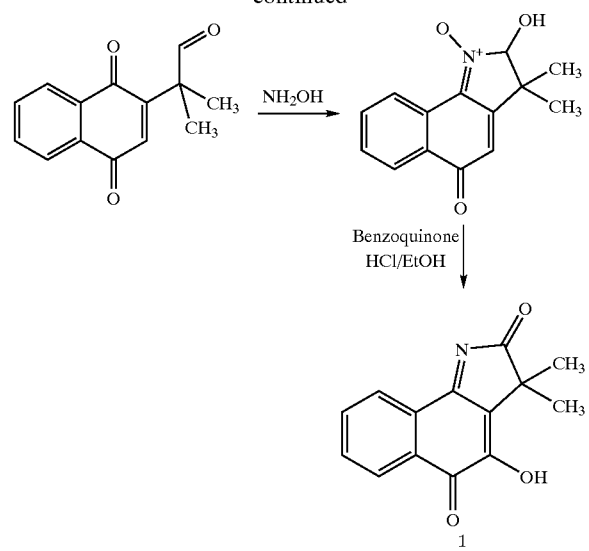

SCHEME 2

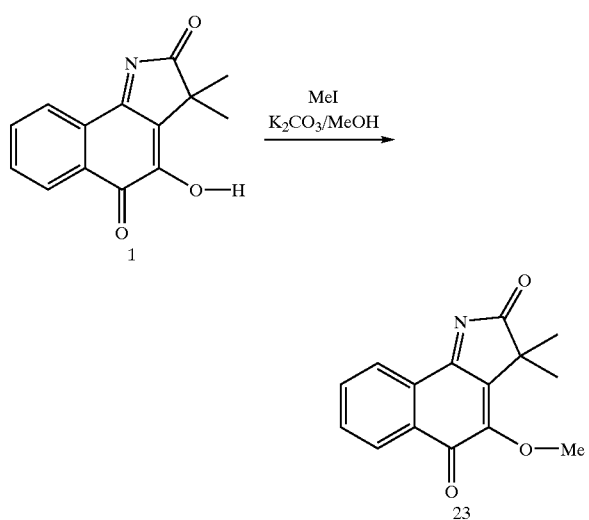

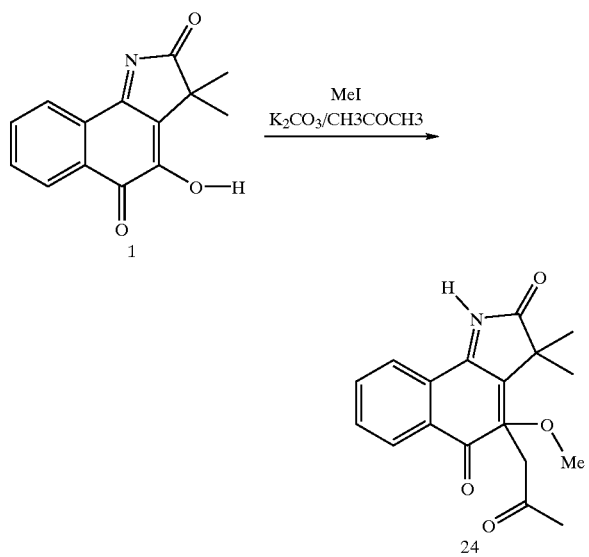

-continued

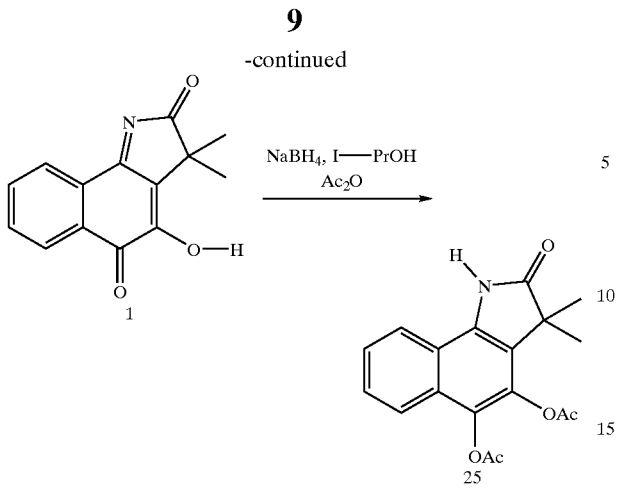

The invention will now be described in more details in the following Examples, which however should not be construed as limiting the invention. In the following examples, column chromatography was carried out using either normal glass columns and compressed air or pumps and fractions collectors. The packing materials used were Merck Silica Gel 60 (230–400 mesh) or YMC-GFL Silica 60 Å S-50 Mesh. $^1$H NMR and $^{13}$C NMR were recorded on a Varian at 500 MHz and at 125.7 MHz, respectively. $^1$H NMR and $^{13}$C NMR spectra were referenced to residual solvent or to tetramethylsilane as internal standard. EI MS spectra were obtained on Micromass Quattro I instrument. Elementary analyses were performed at a Vario EL instrument (Elementar Analysensysteme GmbH, Hanau, Germany).

EXAMPLES

I) Preparation of 6-Hydroxynaphthoquinone (compound 2)

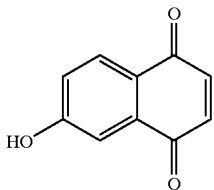

1,6-Dihydroxynaphtalene from Aldrich (3.0 g, 18.7 mmol) was dissolved in a mixture of MeOH (150 mL), $KH_2PO_4$-solution (0.167 M, 150 mL) and water (200 mL), and Potassium nitrosodisulfonate (Fremy's salt) (12.0 g, 44.7 mmol) was added. The mixture was stirred at room temperature 2 h. The reaction mixture was put in refrigerator and then filtered. Yield 3.0 g. $^1$H NMR (400 MHz, $CD_3OD$) δ 6.90 (d, 2 H), 7.12 (dd, 1 H), 7.34 (d, 1 H), 7.92 (d, 1 H).

II) Preparation of 2-(6-Hydroxy-1,4-dioxo-1,4-dihydro-2-naphthalenyl)-2-methylpropanal (compound 3)

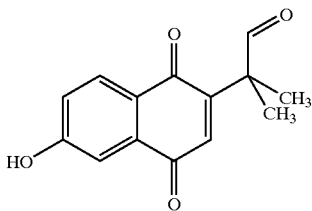

6-Hydroxynaphthoquinone (compound 2 prepared in step I above) (0.74 g, 2.35 mmol) was dissolved in 75% MeOH (30 mL) and powdered $FeCl_3 \cdot 6H_2O$ (1.65 g, 6.1 mmol) was added. The mixture was stirred for 4 h. The solvent was evaporated and the crude product (compound 3) was purified on silica gel with hexane:EtOAc 4:1. Yield: 0.27 g (47%). $^1$H NMR (400 MHz, Acetone-$d_6$) δ 1.36 (s, 6 H), 6.90 (s, 1 H), 7.24 (dd, 1 H), 7.39 (d, 1 H), 7.94 (d, 1 H), 9.64 (s, 1 H).

III) Preparation of 2-(5-Hydroxy-1,4-dioxo-1,4-dihydro-2-naphthalenyl)-2-methylpropanal (compound 4)

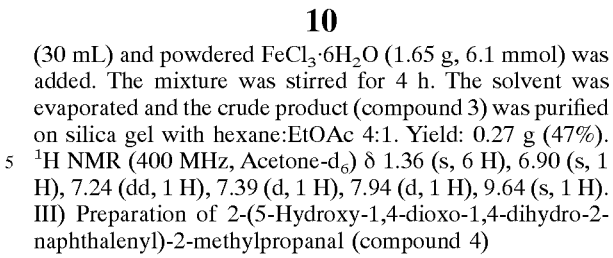

Compound 4 was prepared from 5-hydroxyquinone according to the procedure used for the preparation of compound 3. Yield: 2.11 g (60%). $^1$H NMR (400 MHz, $CDCl_3$) δ 1.43 (s, 6 H), 6.91 (s, 1 H), 7.27 (m, 1 H), 7.60–7.68 (m, 2 H), 9.72 (s, 1 H), 11.76 (s, 1 H).

Example 1

Preparation of 7-Butoxy-4-hydroxy-3,3-dimethyl-2H-benzo[g]indole-2,5(3H)-dione (compound 7)

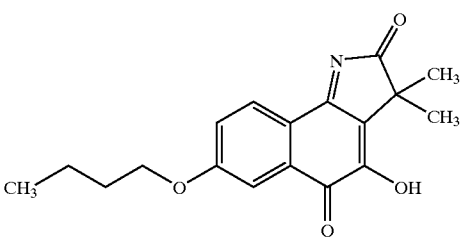

Step (i): Preparation of 2-(6-Butoxy-1,4-dioxo-1,4-dihydro-2-naphthalenyl)-2-methylpropanal (compound 5)

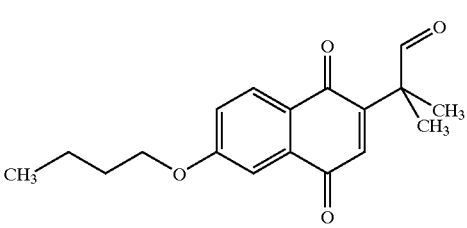

A mixture of 2-(6-Hydroxy-1,4-dioxo-1,4-dihydro-2-naphthalenyl)-2-methylpropanal (compound 3 prepared in step II above) (125 mg, 0.52 mmol) and freshly prepared $Ag_2O$ (240 mg, 1.04 mmol) in $CH_3CN$ was ultrasonicated for 2 min to disperse the silver salt. Iodobutane (120 μL, 1.05 mmol) was added and the mixture was stirred over night at room temperature. The mixture was filtered on Celite and was washed with EtOAc. The crude product was purified on silica gel with hexane:EtOAc 4:1 but failed to yield pure material. The product was further purified on RP-HPLC. Yield: 53 mg (34%). $^1$H NMR (400 MHz, $CDCl_3$) δ 0.99 (tr., 3H), 1.40 (s, 6 H), 1.52 (sext., 2 H), 1.82 (quint., 2 H), 4.11 (tr., 2H), 6.87 (s, 1 H), 7.18 (dd, 1 H), 7.48 (d, 1 H), 8.00 (dd, 1 H), 9.72 (s, 1 H).

Step (ii): Preparation of 7-Butoxy-2-hydroxy-3,3-dimethyl-2,3-dihydro-5H-benzo[g]indol-5-one 1-oxide (compound 6)

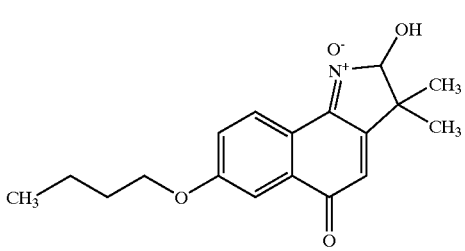

To a solution of 2-(6-Butoxy-1,4-dioxo-1,4-dihydro-2-naphthalenyl)-2-methylpropanal (compound 5 prepared in step (I) above) (53 mg, 0.18 mmol) in MeOH (5 mL) and water (0.5 mL), 50% $NH_2OH$ in water solution (17 μL, 0.28 mmol) was added. The mixture was stirred 3 h at room temp and the solvent was evaporated. The crude product was fairly pure and was taken into the next step without further purification. Yield: 52 mg (92%). $^1H$ NMR (400 MHz, $CDCl_3$) δ 0.99 (tr., 3H), 1.38 (s, 3H), 1.52 (s, 3 H), 1.55 (m, 2 H), 1.84 (quint., 2H), 4.13 (tr., 2H), 5.31 (s, 1 H), 6.43 (s, 1H), 7.24 (d, 1 H), 7.73 (d, 1 H), 9.07 (d, 1 H).

Step (iii): Preparation of the title compound 7-Butoxy-4-hydroxy-3,3-dimethyl-2H-benzo[g]indole-2,5(3H)-dione (compound 7)

A solution of 7-Butoxy-2-hydroxy-3,3-dimethyl-2,3-dihydro-5H-benzo[g]indol-5-one 1-oxide (compound 6 prepared in step (ii) above)(13 mg, 0.036 mmol) in EtOH (2 mL) with conc. HCl in EtOH (0.5 mL) was heated at 60° for 1 h. The yellow solution turned red. When no starting material remained, benzoquinone (39 mg, 0.36 mmol) was added and the mixture was heated 1 h. The solvent was evaporated and the crude product was purified on RP-HPLC. Yield. 12 mg. (24%). $^1H$ NMR (400 MHz, $CDCl_3$) δ 1.00 (tr., 3H), 1.51 (m, 2 H), 1.55 (s, 6 H), 1.82 (m, 2 H), 4.10 (tr., 2H), 7.20 (dd, 1 H), 7.46 (d, 1 H), 7.70 (d, 1 H), 9.62 (br.s, 1 H). MS (EI) m/z 313 ($M^+$).

Example 2

Preparation of 9-(Benzyloxy)-4-hydroxy-3,3-dimethyl-2H-benzo[g]indole-2,5(3H)-dione (compound 10)

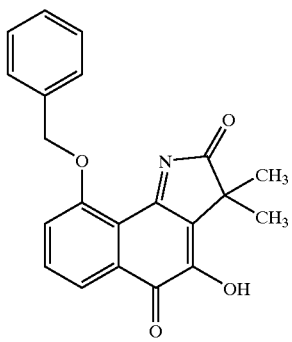

Compound 10 was prepared according the procedure described for Example 1.

Step (i): Preparation of 2-[8-(Benzyloxy)-1,4-dioxo-1,4-dihydro-2-naphthalenyl]-2-methylpropanal (compound 8)

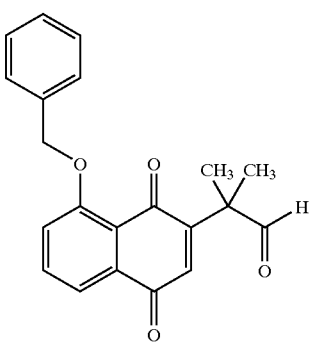

Benzyl bromide was used as reagent. Yield: 209 mg (62%). $^1H$ NMR (400 MHz, Acetone-$d_6$) δ 1.37 (s, 6 H), 5.35 (s, 2 H), 6.89 (s, 1 H), 7.31 (m, 1 H), 7.39 (tr, 2 H), 7.61 (m, 3 H), 7.66 (d, 1 H), 7.77 (m, 1 H), 9.65 (s, 1 H).

Step (ii): Preparation of 9-(Benzyloxy)-2-hydroxy-3,3-dimethyl-2,3-dihydro-5H-benzo[g]indol-5-one 1-oxide compound 9)

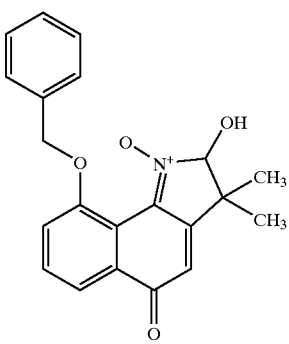

Yield: 70 mg (40%). $^1H$ NMR (400 MHz, $CDCl_3$) δ 1.36 (s, 3 H), 1.46 (s, 3 H), 5.37 (s, 2 H), 5.77 (br.s, 1H), 6.38 (s, 1 H), 7.30 (d, 1 H), 7.37 (m, 3 H), 7.56 (m, 3 H), 7.88 (d, 1 H).

Step (iii): Preparation of the title compound 9-(Benzyloxy)-4-hydroxy-3,3-dimethyl-2H-benzo[g]indole-2,5(3H)-dione (compound 10)

Yield: 37 mg (62%). $^1H$ NMR (400 MHz, $CDCl_3$) δ 1.48 (s, 6 H), 5.31 (s, 2 H), 7.31 (d, 1 H), 7.44 (m, 5 H), 7.53 (tr, 1 H), 7.85 (d, 1 H), 8.98 (br.s, 1 H). MS (EI) m/z 347 ($M^+$)

Example 3

Preparation of 4-Hydroxy-9-isobutoxy-3,3-dimethyl-2H-benzo[g]indole-2,5(3H)-dione (Compound 13)

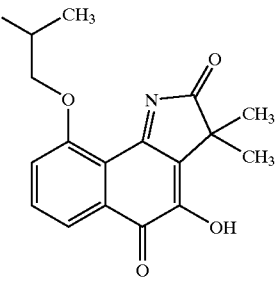

Compound 13 was prepared according the procedure used for Example 1. Iodo-2-methylpropane was used as reagent.

Step (i): Preparation of 2-(8-Isobutoxy-1,4-dioxo-1,4-dihydro-2-naphthalenyl)-2-methylpropanal (compound 11)

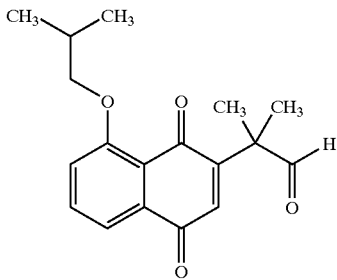

Yield: 120 mg (40%). $^1$H NMR (400 MHz, CDCl$_3$) δ 1.07 (s, 3 H), 1.09 (s, 3 H), 1.38 (s, 6 H), 2.21 (sept., 1 H), 3.88 (d, 2 H), 6.83 (s, 1 H), 7.28 (dd, 1 H), 7.64 (tr, 1 H), 7.68 (dd, 1 H), 9.69 (s, 1 H).

Step (ii): Preparation of 2-Hydroxy-9-isobutoxy-3,3-dimethyl-2,3-dihydro-5H-benzo[g]indol-5-one 1-oxide (compound 12)

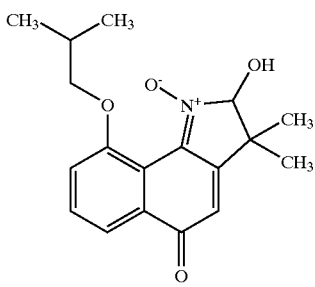

Yield: 27 mg (25%). $^1$H NMR (400 MHz, CDCl$_3$) δ 0.99 (s, 3 H), 1.01 (s, 3 H), 1.31 (s, 3 H), 1.43 (s, 3 H), 2.21 (nonett, 1 H), 3.82 (dd, 1 H), 3.91 (dd, 1 H), 5.21 (s, 1 H), 6.31 (s, 1 H), 7.15 (d, 1 H), 7.50 (tr, 1 H), 7.78 (dd, 1 H).

Step (iii): Preparation of the title compound 4-Hydroxy-9-isobutoxy-3,3-dimethyl-2H-benzo[g]indole-2,5(3H)-dione (compound 13)

Yield. 8 mg (30%). $^1$H NMR (400 MHz, CDCl$_3$) δ 1.12 (s, 3 H), 1.14 (s, 3 H), 1.52 (s, 6 H), 2.27 (nonett, 1 H), 4.00 (d, 1 H), 7.24 (dd, 1 H), 7.55 (tr, 1 H), 7.85 (dd, 1 H), 8.97 (br.s, 1 H). MS (EI) m/z 313 (M$^+$)

Example 4
Preparation of 4-Hydroxy-3,3-dimethyl-9-(2-phenylethoxy)-2H-benzo[g]indole-2,5(3H)-dione (compound 16)

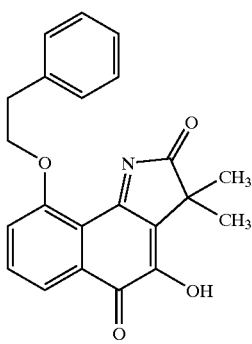

Compound 16 was prepared according the procedure used for Example 1.

Step (i): Preparation of 2-[1,4-Dioxo-8-(2-phenylethoxy)-1,4-dihydro-2-naphthalenyl]-2-methylpropanal (compound 14)

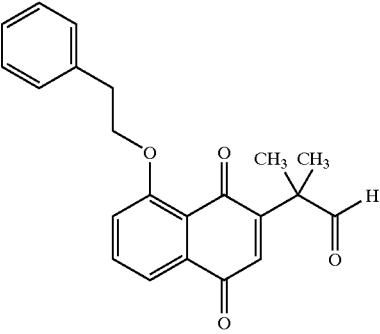

(2-Iodoethyl) benzene was used as reagent. Yield: 100 mg (35%). $^1$H NMR (400 MHz, CDCl$_3$) δ 1.39 (s, 6 H), 3.20 (tr, 2 H), 4.29 (tr., 2 H), 6.83 (s, 1 H), 7.23 (m, 2 H), 7.31 (m, 3 H), 7.35 (m, 1 H), 7.60 (tr., 1 H), 7.67 (dd, 1 H), 9.71 (s, 1 H).

Step (ii): Preparation of 2-Hydroxy-3,3-dimethyl-9-(2-phenylethoxy)-2,3-dihydro-5H-benzo[g]indol-5-one 1-oxide (compound 15)

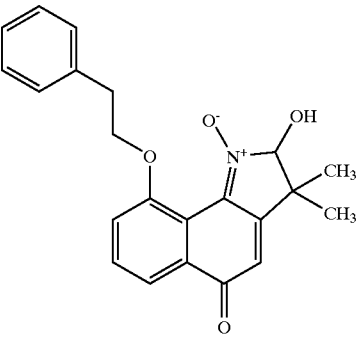

Yield: 13 mg (14%). $^1$H NMR (400 MHz, CDCl$_3$) δ 1.38 (s, 3 H), 1.47 (s, 3 H), 3.24 (m, 2 H), 4.32 (m, 1 H), 4.43 (m, 1 H), 5.27 (s, 1 H), 6.35 (s, 1 H), 7.22 (m, 1 H), 7.26–7.39 (m, 5 H), 7.54 (tr., 1 H), 7.84 (d, 1 H).

Step (iii): Preparation of the title compound 4-Hydroxy-3,3-dimethyl-9-(2-phenylethoxy)-2H-benzo[g]indole-2,5 (3H)-dione (compound 16)

Yield: 5 mg. (40%). $^1$H NMR (400 MHz, CDCl$_3$) δ 1.46 (s, 6 H), 3.23 (tr., 2 H), 4.50 (tr., 2 H), 7.26 (dd, 1 H), 7.33 (m, 3 H), 7.42 (m, 2 H), 7.54 (tr., 1 H), 7.82 (dd, 1 H), 8.71 (br.s, 1 H). MS (EI) m/z 361 (M$^+$)

Example 5
Preparation of 4-Hydroxy-9-ethoxy-3,3-dimethyl-2H-benzo[g]indole-2,5(3H)-dione (compound 19)

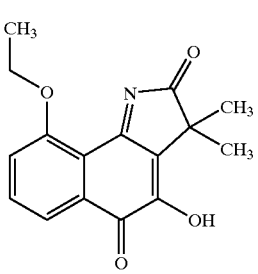

Compound 19 was prepared according the procedure used for Example 1.

Step (i): Preparation of 2-(8-ethoxy-1,4-dioxo-1,4-dihydro-2-naphthalenyl)-2-methylpropanal (compound 17)

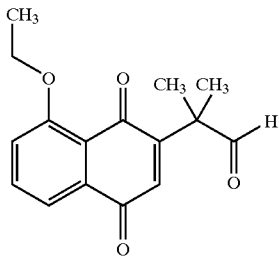

Iodoethane was used as reagent. Yield: 380 mg (93%). $^1$H NMR (400 MHz, CDCl$_3$) δ 1.38 (s, 6 H), 1.43 (t, 3 H), 3.89 (q, 2 H), 6.83 (s, 1 H), 7.28 (dd, 1 H), 7.64 (tr, 1 H), 7.68 (dd, 1 H), 9.69 (s, 1 H).

Step (ii): Preparation of 2-Hydroxy-9-ethoxy-3,3-dimethyl-2,3-dihydro-5H-benzo[g]indol-5-one 1-oxide (compound 18)

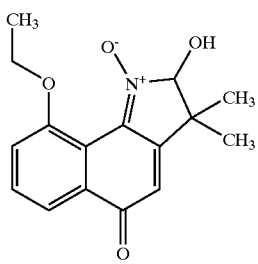

Yield: 130 mg (60%). $^1$H NMR (400 MHz, CDCl$_3$) δ 1.31 (s, 6 H), 1.35 (t, 3 H), 3.87 (q, 2 H), 5.21 (d, 1 H), 6.31 (s, 1 H), 7.15 (d, 1 H), 7.50 (tr, 1 H), 7.78 (dd, 1 H).

Step (iii): Preparation of the title compound 4-Hydroxy-9-ethoxy-3,3-dimethyl-2H-benzo[g]indole-2,5(3H)-dione (compound 19)

Yield. 65 mg (30%). $^1$H NMR (400 MHz, CDCl$_3$) δ 1.36 (s, 6 H), 1.37 (s, 3 H), 3.90 (q, 1 H), 7.24 (dd, 1 H), 7.55 (tr, 1 H), 7.85 (dd, 1 H), 8.97 (br.s, 1 H). MS (EI) m/z 285 (M$^+$)

Example 6

Preparation of 2-[(4-Hydroxy-3,3-dimethyl-2,5-dioxo-3,5-dihydro-2H-benzo[g]indol-9-yl)oxy]acetamide (compound 22)

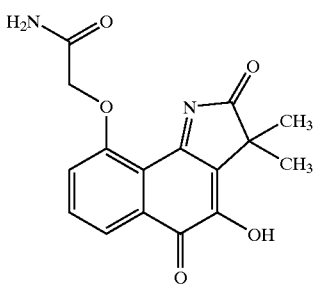

Compound 22 was prepared according the procedure used for Example 1.

Step (i): Preparation of 2-{[7-(1,1-Dimethyl-2-oxoethyl)-5,8-dioxo-5,8-dihydro-1-naphthalenyl]oxy}acetamide (compound 20)

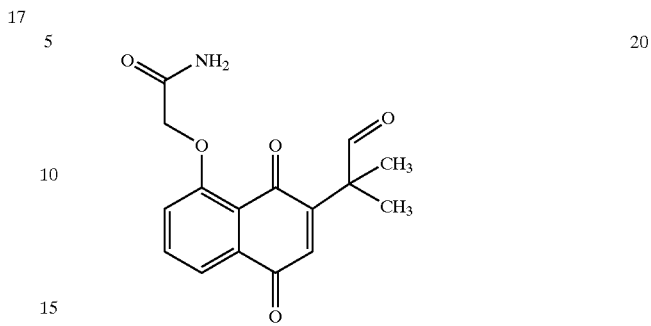

Acrylamide was used as reagent. Yield: 67 mg (27%). $^1$H NMR (400 MHz, Acetone-d$_6$) δ 1.38 (s, 6 H), 4.63 (s, 2 H), 6.95 (s, 1 H), 7.56 (d, 1 H), 7.73 (d, 1 H), 7.86 (tr., 1 H), 9.65 (s, 1 H).

Step (ii): Preparation of 2-[(2-Hydroxy-3,3-dimethyl-1-oxido-5-oxo-3,5-dihydro-2H-benzo[g]indol-9-yl)oxy]acetamide (compound 21)

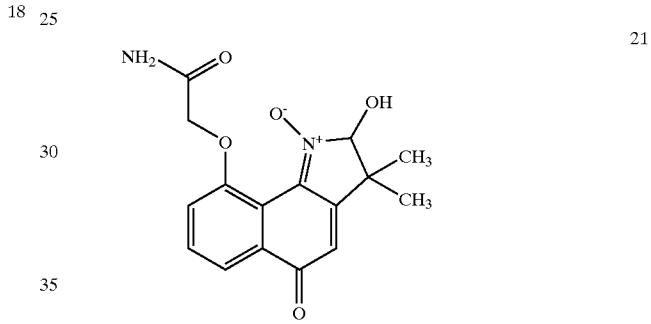

Yield: 70 mg crude product has been used to obtain the final compound. MS (EI) m/z 314 (M$^+$)

Step (iii): Preparation of the title compound 2-[(4-Hydroxy-3,3-dimethyl-2,5-dioxo-3,5-dihydro-2H-benzo[g]indol-9-yl)oxy]acetamide (Compound 22)

Yield: 7 mg. (10%). $^1$H NMR (400 MHz, DMSO-d$_6$) δ 1.34 (s, 6 H), 4.83 (s, 2 H), 7.36 (tr., 1 H), 7.54 (br.s, 1 H), 7.67 (m, 2 H), 7.77 (br.s, 1 H), 11.25 (br.s, 1 H). MS (EI) m/z 314 (M$^+$)

Example 7

Preparation of 4-methoxy-3,3-dimethyl-2H-benzo[g]indole-2,5(3H)-dione (compound 23)

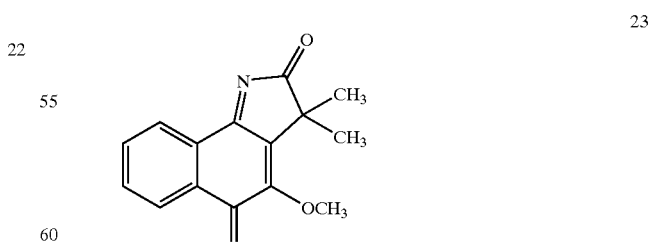

To a solution of 4-hydroxy-3,3-dimethyl-2H-benzo[g]indole-2,5(3H)-dione (compound 1) (0.1 g, 0.415 mmol) in MeOH (5 mL) was added K$_2$CO$_3$ (0.132 g, 0.96 mmol) while stirring at RT. After 10 min. MeI (100 μL, 0.228 g, 1.6 mmol) was added via a syringe and the mixture was allowed to stirred over night. The solvent was removed in vacuum and the solid was dissolved in CHCl₃, filtered and purified by prep. HPLC (SF/CHCl₃). Yield: 0.051 mg (50%). ¹H NMR (400 MHz, CDCl₃) δ 1.48 (s, 6 H), 3.68 (s, 3 H), 7.58 (t, 1 H), 7.68 (t, 1 H), 8.02 (d, 1 H), 8.23 (d, 1 H). MS (CI) m/z: 256.31 (M+1).

Example 8
Preparation of 4-methoxy-3,3-dimethyl-4-(2-oxopropyl)-1H-benzo[g]indole-2,5(3H,4H)-dione (compound 24)

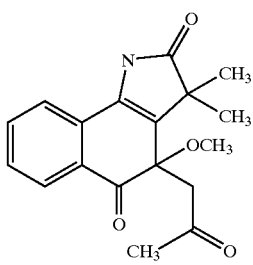

24

To a solution of 4-hydroxy-3,3-dimethyl-2H-benzo[g]indole-2,5(3H)-dione (compound 1) (0.1 g, 0.415 mmol) in acetone (5 mL) was added K₂CO₃ (0.132 g, 0.96 mmol) while stirring at RT. After 10 minutes, MeI (0.058 g, 0,41 mmol) was added via a syringe and the mixture was allowed to stir for 1 h followed by addition of more MeI (0.058 g, 0,41 mmol) and the reaction was stirred over night. The solvent was removed in vacuum and the solid was dissolved in CHCl₃, filtered and purified by preparative HPLC. Yield: 64 mg (50%). ¹H NMR (400 MHz, CDCl₃) δ 1.46 (d, 6 H), 2.12 (s, 3 H), 2.90 (s, 2 H), 3.65 (s, 3 H), 7.42 (t, 1 H), 7.55 (t, 1 H), 7.78 (d, 1 H), 7.94 (d, 1 H): MS (CI) m/z 314.36 (M+1).

Example 9
Preparation of 4-(acetyloxy)-3,3-dimethyl-2-oxo-2,3-dihydro-1H-benzo[g]indol-5-yl Acetate (compound 25)

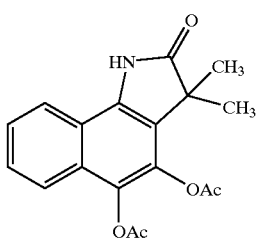

25

To a solution of 4-hydroxy-3,3-dimethyl-2H-benzo[g]indole-2,5(3H)-dione (0.030 g, 0.124 mmol) in i-PrOH (0.5 mL) was added NaBH₄ (0.020 g, 0.52 mmol) while stirring at RT. After 5 minutes, Ac₂O (100 μL, 0.1 g, 0,98 mmol) was added via a syringe and the mixture was allowed to stir for 1 h followed by addition of more NaBH₄ (0.020 g, 0.52 mmol) and stirring over night. The solvent was removed in vacuum and the solid was dissolved in CHCl₃, filtered and purified by prep. HPLC (RP). Yield: 0.016 mg (40%). ¹H NMR (400 MHz, CDCl₃) δ 1.50 (brs, 6 H), 2.35 (appd, 6 H), 7.47 (m, 2 H), 7.68 (d, 1 H), 7.85 (d, 1 H), 10.05 (brs, 1 H). MS (CI) m/z: 328.36 (M+1).

Pharmaceutical Compositions

The novel compounds according to the present invention may be administered orally, intranasally, transdermally, subcutaneously, parenterally, intramuscularly, as well as intravenously. Oral administration is the preferred route.

The dosage will depend on the route of administration, the severity of the disease, age and weight of the patient, and other factors normally considered by the attending physician when determining the individual regimen and dosage level as the most appropriate for a particular patient.

Either solid or fluid dosage forms can be prepared for oral administration. Solid compositions, such as compressed tablets, are prepared by mixing the compounds of the invention with conventional ingredients such as talc, magnesium stearate, dicalcium phosphate, magnesium aluminum silicate, calcium sulfate, starch, lactose, acacia, methyl cellulose, or functionally similar pharmaceutical diluents and carriers. Capsules are prepared by mixing the compounds of this invention with an inert pharmaceutical diluent and placing the mixture into an appropriately sized hard gelatin capsule. Soft gelatin capsules are prepared by machine encapsulation of a slurry of the compounds of this invention with an acceptable inert oil such as vegetable oil or light liquid petrolatum.

Syrups are prepared by dissolving compounds of the invention in an aqueous vehicle and adding sugar, aromatic flavoring agents and preservatives. Elixirs are prepared using a hydroalcoholic vehicle such as ethanol, suitable sweeteners such as sugar or saccharin and an aromatic flavoring agent. Suspensions are prepared with an aqueous vehicle and a suspending agent such as acacia, tragacanth, or methyl cellulose.

When the compounds of the invention are administered parenterally, they can be given by injection or by intravenous infusion. Parenteral solutions are prepared by dissolving the compounds of the invention in aqueous vehicle and filter sterilizing the solution before placing in a suitable sealable vial or ampule. Parenteral suspensions are prepared in substantially the same way except a sterile suspension vehicle is used and the compounds of the present invention are sterilized with ethylene oxide or suitable gas before it is suspended in the vehicle.

Thus, a further aspect of the present invention is a pharmaceutical composition comprising a compound of formula I, formula Ia, or formula Ib, supra, as active ingredient, together with a pharmacologically and pharmaceutically acceptable carrier. It is preferred to use pharmaceutically inert carriers which may be solid or liquid. Solid form preparations include but is not limited to powders, tablets, dispersible granules, capsules etc. A skilled person within the formulation field will readily know which carrier to use for the specific circumstance when formulating a composition in accordance with the present invention.

Pharmaceutically acceptable salts of a compound of formula I, formula Ia, or formula Ib, supra, which are within the scope of the present invention, may be formed from organic and inorganic acids. Examples of such salts are hydrochloride salts, tosylate salts, citrate salts, maleate salts, acetate salts, hydrobromide salts, malate salts, stearate salts, aluminium salts, lithium salts, calcium salts, and magnesium salts. This list should however not in any way be regarded as exhaustive. The hydrochloride salts are preferred.

Biological Evaluation

The compound 4-hydroxy-3,3-dimethyl-2H-benzo[g]indole-2,5(3H)-dione, which is commercially available from Labotest in Germany, was tested for the medical indications claimed herein, together with other compounds within the scope of the present invention.

Methods

Expression and Purification of Recombinant Human PTPs

Human PTP1B (amino acid residues 1–298, cloned from a human placental library), without the GST tag and thrombin cleavage site, was inserted into a pMB replicon and transformed into E. coli BL21(DE3), a strain containing a chromosomal copy of the gene for T7 RNA polymerase under control of a lacUV5 promoter. Expression of PTP1B was induced with isopropyl thiogalactose and cells were lysed in lysis buffer comprising 50 mM Tris-HCl pH 7.5, 10% glycerol, 1 mM EDTA, 3 mM DTT, 3 mM $MgCl_2$, and 0.2 mg/ml lysozyme with 1 mg/ml DNAse I. The soluble protein was purified by ion exchange, hydrophobic interaction and gel exclusion chromatography for use in assays to identify PTP1B inhibitors. The plasmid pGEX2K-SHP2 which encoded the catalytic domain of human SHP-2 (residues 252–529) was used to transform E. coli cells. After induction of protein expression, cells were lysed in PBS containing 1% Triton X100 and lysozyme (2 mg/ml). Recombinant protein was purified by glutathione sepharose 4B chromatography followed by Superdex 200 size exclusion chromatography. Recombinant proteins were stored at −70° C. until used. Recombinant T cell PTP (TCPTP) and LAR were purchased from New England Biolabs.

Measurement of PTP Activity

Human PTP1B activity was measured using p-nitrophenol phosphate (pNPP) as substrate in a 96-well microtiter plate format. An assay pH of 7.2 is used for standard assays (measured extinction coefficient=9800 at pH 7.2).

Standard assays were conducted at room temperature in a total volume of 0.2 ml that contains Hepes buffer (50 mM, pH 7.2), NaCl (50 mM), EDTA (1 mM), DTT (1 mM), bovine serum albumin (1 mg/ml), pNPP (1.25 mM) and PTP1B (500 ng/ml, 13.5 nM). A master plate was set up for each compound in which a stock solution of compound in DMSO (19 mM or 1 mM) was diluted 1 to 10 with assay buffer in column 1 (giving a 1 mM or 100 µM concentration). Substances were subsequently diluted serially by two thirds in all columns across the plate. For enzyme assays, 20 µl of each diluted compound was removed to a new plate and diluted to 200 µl (final volume) with 160 µl pNPP solution and 20 µl PTP1B solution. Reactions were thus started immediately and were stopped after 60 minutes by addition of 100 µl 0.1N NaOH. The $OD^{405}$ was subsequently measured. Two wells on each plate contained DMSO controls and two wells contained sodium orthovanadate (2 mM) which inhibits PTP1B-catalyzed hydrolysis of pNPP completely. Data were corrected for background absorbance by the subtraction of the optical densities from a no-enzyme control plate and were expressed as percent inhibition relative to the average of the vanadate controls measured on the same microtiter plate. The activity of the other PTPs was determined in a similar fashion except that the concentration of pNPP was varied according to the Km values for individual enzymes (0.6 mM for TCPTP and 6.25 mM for each of SHP-2 and LAR) and the buffer used for TCPTP was 25 mM Tris-HCl pH 7.2.

Cell-based Analysis of Compound Activity

The effects of compounds on the phosphorylation status of the insulin receptor was measured using L6 muscle cells expressing the receptor endogenously. L6 myocytes were cultured in α-MEM with 10% foetal bovine serum and antibiotics. Cells were differentiated into myotubes in 24-well plates by culturing for 10 days in medium containing 2% serum. The medium was refreshed on alternate days and 0.24 mg/ml cytidine was included from day 7 to stop any remaining cycling cells. Cells were starved of serum overnight prior to use. Cells were pretreated with compound at approximately five times the $IC_{50}$ for inhibition of PTP1B for 30 minutes, prior to being stimulated with insulin (25 nM) for five minutes. Cells were lysed in buffer comprising 25 mM Tris-HCl pH 7.4, 150 mM NaCl, 1 mM EDTA, 1 mM EGTA, 1% Nonidet-40, 0.25% sodium deoxycholate, 1 mM sodium orthovanadate, 10 mM β-glycerophosphate, 5 mM sodium pyrophosphate and protease inhibitors. Cleared lysates were stored at −70° C. until used.

Insulin receptor phosphorylation was assessed using a lanthanide-based fluorescent assay (DELFIA). An anti-insulin receptor antibody was captured on the wells of a 96-well plate using an anti-rabbit IgG antibody. After incubation with lysates containing between 100–250 µg protein which was consistent for all wells in a single experiment, phosphate on the receptor was detected with a biotinylated anti-phosphotyrosine antibody (PY99B from Santa Cruz) and europium-labelled streptavidin.

Results $IC_{50}$ values were determined for all compounds against each of four PTPs (PTP1B, SHP-2, LAR and TCPTP). Compounds were active across a wide range of concentrations from 100 nM to 50 µM.

Representative compounds from across the series were analysed in cell-based assays in which effects on insulin-stimulated auto-phosphorylation of the insulin receptor was determined. Compounds caused statistically significant increases in receptor phosphorylation by about 20% to about 70%.

What is claimed is:

1. A compound of formula I, formula Ia, or formula Ib

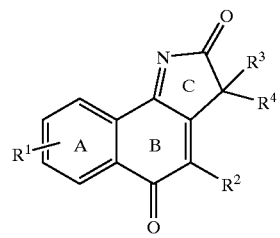

I

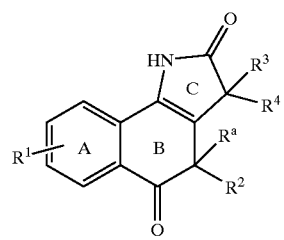

Ia

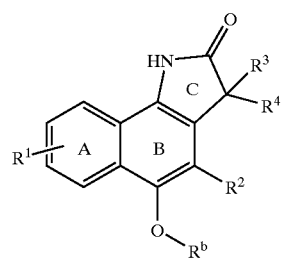

Ib wherein $R^1$ is (i) hydrogen;

(ii) linear or branched $C_1$–$C_6$ alkoxy;

(ii) —O—($C_1$-$C_6$ alkyl)—Q, where the alkyl group is linear or branched, and Q is phenyl, naphthyl, or a heterocycle having 5 to 10 ring atoms, where at least one of the ring atoms is O, N, or S;

(iv)

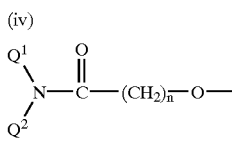

where n is an integer 1 or 2, and each of $Q^1$ and $Q^2$ is independently hydrogen or $C_1$-$C_6$ alkyl, where the alkyl group is linear or branched; or (v)

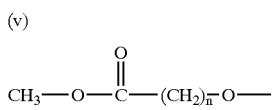

where n is an integer 1 or 2;
$R^2$ is
(i) hydroxy;
(ii) linear or branched $C_1$-$C_6$ alkoxy;
(iii) —O—CO—($C_1$-$C_6$ alkyl), where the alkyl group is linear or branched; or
(iv) —O—CO-phenyl or —O—CO-naphthyl;
each of $R^3$ and $R^4$ is independently
(i) linear or branched $C_1$-$C_6$ alkyl; or
(ii) cyclopentane or cyclohexane;
$R^a$ is —$CH_2$—CO—($C_1$-$C_6$ alkyl), where the alkyl group is linear or branched; and
$R^b$ is
(i) —CO—($C_1$-$C_6$ alkyl), where the alkyl group is linear or branched; or
(ii) hydrogen;
provided that the compound 4-hydroxy-3,3-dimethyl-2H-benzo[g]indole-2,5(3H)-dione is excluded;
or a pharmaceutically and pharmacologically acceptable salt or hydrate thereof.

2. The compound of claim 1, said compound having formula I.

3. The compound of claim 1, said compound having formula Ia.

4. The compound of claim 1, said compound having formula Ib.

5. The compound of claim 1, wherein
$R^1$ is linear or branched $C_1$-$C_6$ alkoxy, phenyl-$(CH_2)_n$—O— where n is an integer 1 or 2, or $H_2N$—CO—$CH_2$—O—; and
$R^2$ is linear or branched $C_1$-$C_6$ alkoxy, —O—CO—$(CH_2)_n$—$CH_3$ where n is an integer 0, 1, 2, 3, 4 or 5, —O—CO-phenyl, or —O—CO-naphthyl.

6. The compound of claim 1, wherein
$R^2$ is hydroxy, linear or branched $C_1$-$C_3$ alkoxy, or —O—CO—$(CH_2)_n$—$CH_3$ where n is an integer 0, 1, 2, or 3.

7. The compound of claim 6, wherein $R^2$ is hydroxy.

8. The compound of claim 6, wherein
$R^1$ is hydrogen, linear or branched $C_1$-$C_6$ alkoxy, phenyl-$(CH_2)_n$—O— where n is an integer 1 or 2, or $H_2N$—CO—$CH_2$—O—; and
each of $R^3$ and $R^4$ is independently linear or branched $C_1$-$C_3$ alkyl.

9. The compound of claim 1, wherein
$R^1$ is hydrogen, linear or branched ethoxy, propoxy, or butoxy; phenyl-$(CH_2)_n$—O— where n is an integer 1 or 2; or $H_2N$—CO—$CH_2$—O—;
$R^2$ is hydroxy, methoxy, or —O—CO—$CH_3$; and
$R^3$ and $R^4$ are each methyl.

10. The compound of claim 1, wherein $R^a$ is —$CH_2$—CO—$(CH_2)_n$—$CH_3$ where n is an integer 0, 1, 2, 3, 4 or 5.

11. The compound of claim 1, wherein $R^a$ is —$CH_2$—CO—$CH_3$.

12. The compound of claim 1, wherein $R^b$ is —CO—$(CH_2)_n$—$CH_3$ where n is an integer 0, 1, 2, 3, 4 or 5.

13. The compound of claim 1, wherein $R^b$ is —CO—$CH_3$.

14. The compound of claim 1, said compound being:
7-butoxy-4-hydroxy-3,3-dimethyl-2H-benzo[g]indole-2,5(3H)-dione (compound 7);
9-(benzyloxy)-4-hydroxy-3,3-dimethyl-2H-benzo[g]indole-2,5(3H)-dione (compound 10);
4-hydroxy-9-isobutoxy-3,3-dimethyl-2H-benzo[g]indole-2,5(3H)-dione (compound 13);
4-hydroxy-3,3-dimethyl-9-(2-phenylethoxy)-2H-benzo[g]indole-2,5(3H)-dione (compound 16);
4-hydroxy-9-ethoxy-3,3-dimethyl-2H-benzo[g]indole-2,5(3H)-dione (compound 19);
2-[(4-hydroxy-3,3-dimethyl-2,5-dioxo-3,5-dihydro-2H-benzo[g]indol-9-yl)oxy]acetamide (compound 22);
4-methoxy-3,3-dimethyl-2H-benzo[g]indole-2,5(3H)-dione (compound 23);
4-methoxy-3,3-dimethyl-4-(2-oxopropyl)-1H-benzo[g]indole-2,5(3H,4H)-dione (compound 24); or
4-(acetyloxy)-3,3-dimethyl-2-oxo-2,3-dihydro-1H-benzo[g]indol-5-yl acetate (compound 25).

15. A hydrochloride salt or tosylate salt of a compound of claim 1.

16. A hydrochloride salt of a compound of claim 1.

17. A hydrochloride salt of a compound of claim 9.

18. A hydrochloride salt of a compound of claim 14.

19. A pharmaceutical composition comprising a compound of claim 1 and a pharmacologically and pharmaceutically acceptable carrier.

20. A pharmaceutical composition comprising a compound of claim 9 and a pharmacologically and pharmaceutically acceptable carrier.

21. A pharmaceutical composition comprising a compound of claim 14 and a pharmacologically and pharmaceutically acceptable carrier.

22. A method for treating type 2 diabetes mellitus, comprising administering to a subject in need thereof an effective amount of a compound of formula I, formula Ia, or formula Ib:

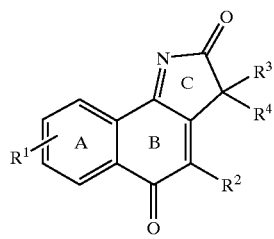

-continued

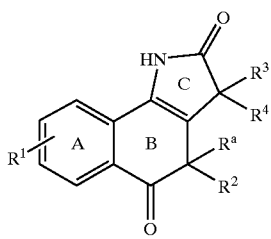

Ia

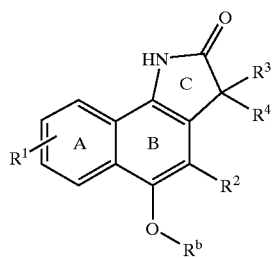

Ib wherein

R¹ is
(i) hydrogen;
(ii) linear or branched $C_1$–$C_6$ alkoxy;
(ii) —O—($C_1$–$C_6$ alkyl)—Q, where the alkyl group is linear or branched, and Q is phenyl, naphthyl, or a heterocycle having 5 to 10 ring atoms, where at least one of the ring atoms is O, N, or S;

(iv)

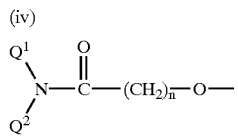

where n is an integer 1 or 2, and each of $Q^1$ and $Q^2$ is independently hydrogen or $C_1$–$C_6$ alkyl, where the alkyl group is linear or branched; or (v)

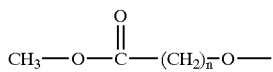

where n is an integer 1 or 2;

R² is
(i) hydroxy;
(ii) linear or branched $C_1$–$C_6$ alkoxy;
(iii) —O—CO—($C_1$–$C_6$ alkyl), where the alkyl group is linear or branched, or
(iv) —O—CO-phenyl or —O—CO-naphthyl;

each of R³ and R⁴ is independently
(ii) linear or branched $C_1$–$C_6$ alkyl; or
(ii) cyclopentane or cyclohexane;

$R^a$ is —CH₂—CO—($C_1$–$C_6$ alkyl), where the alkyl group is linear or branched; and $R^b$ is
(i) —CO—($C_1$–$C_6$ alkyl), where the alkyl group is linear or branched; or
(ii) hydrogen;

or a pharmaceutically and pharmacologically acceptable salt or hydrate thereof.

23. A method for treating type 2 diabetes mellitus, comprising administering to a subject in need thereof an effective amount of a compound of claim 9.

24. A method for treating type 2 diabetes mellitus, comprising administering to a subject in need thereof an effective amount of a compound of claim 14.

* * * * *